US010517747B2

(12) United States Patent
Kim et al.

(10) Patent No.: US 10,517,747 B2
(45) Date of Patent: Dec. 31, 2019

(54) CANNULA CUT STENT WITH CLOSED END CELL GEOMETRY

(71) Applicant: Cook Medical Technologies LLC, Bloomington, IN (US)

(72) Inventors: Seoggwan Kim, West Lafayette, IN (US); Richard A. Swift, South Bend, IN (US); Conor Dillon, County Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 207 days.

(21) Appl. No.: 15/626,467

(22) Filed: Jun. 19, 2017

(65) Prior Publication Data

US 2018/0360630 A1 Dec. 20, 2018

(51) Int. Cl.
*A61F 2/915* (2013.01)
*A61F 2/82* (2013.01)
*A61F 2/958* (2013.01)

(52) U.S. Cl.
CPC ............ *A61F 2/915* (2013.01); *A61F 2/958* (2013.01); *A61F 2002/825* (2013.01); *A61F 2002/91558* (2013.01); *A61F 2002/91566* (2013.01); *A61F 2002/91575* (2013.01); *A61F 2210/0014* (2013.01); *A61F 2250/0036* (2013.01)

(58) Field of Classification Search
CPC .... A61F 2/95; A61F 2/915; A61F 2002/9155; A61F 2002/91558; A61F 2002/91566; A61F 2002/91575
See application file for complete search history.

(56) References Cited

U.S. PATENT DOCUMENTS

| | | |
|---|---|---|
| 5,925,061 A | 7/1999 | Ogi et al. |
| 6,113,627 A | 9/2000 | Jang |
| 6,203,569 B1 | 3/2001 | Wijay |
| 6,436,133 B1 | 8/2002 | Furst et al. |
| 8,328,864 B2 | 12/2012 | Niermann |
| 8,414,637 B2 | 4/2013 | Chouinard |
| 8,568,471 B2 | 10/2013 | Trollsas et al. |
| 8,603,155 B2 | 12/2013 | Mews et al. |
| 8,663,315 B2 | 3/2014 | Hong et al. |
| 9,028,540 B2 | 5/2015 | Wainwright et al. |
| 9,089,446 B2 | 7/2015 | Li et al. |
| 9,284,637 B2 | 3/2016 | Boyle et al. |
| 2002/0045933 A1 | 4/2002 | Jang |
| 2002/0095207 A1 | 7/2002 | Moriuchi et al. |
| 2004/0088041 A1 | 5/2004 | Stanford |

(Continued)

FOREIGN PATENT DOCUMENTS

| | | |
|---|---|---|
| WO | WO 01/00112 A1 | 1/2001 |
| WO | WO 2001/089417 A1 | 11/2001 |
| WO | WO 2011/103257 A1 | 8/2011 |

OTHER PUBLICATIONS

Communication—Extended European Search Report dated Oct. 24, 2018 for EP 18178614.6-113 (7 pages).

*Primary Examiner* — Tuan V Nguyen
(74) *Attorney, Agent, or Firm* — Brinks Gilson & Lione

(57) ABSTRACT

Disclosed herein is an intraluminal support device including a closed cell design on at least one end of the device. In such a device, the closed cell structure is formed by connecting all peaks of an ultimate ring to all peaks of a penultimate ring, and all valleys of the ultimate ring to all valleys of the ultimate ring. The support device expands evenly due to this structure.

20 Claims, 4 Drawing Sheets

(56) References Cited

U.S. PATENT DOCUMENTS

| | | | |
|---|---|---|---|
| 2004/0230293 A1 | 11/2004 | Yip et al. | |
| 2004/0236399 A1 | 11/2004 | Sundar | |
| 2005/0209670 A1* | 9/2005 | George | A61F 2/95 623/1.11 |
| 2006/0235506 A1* | 10/2006 | Ta | A61F 2/91 623/1.16 |
| 2008/0195193 A1* | 8/2008 | Purdy | A61F 2/91 623/1.16 |
| 2010/0324659 A1* | 12/2010 | Mews | A61F 2/915 623/1.16 |
| 2011/0230957 A1 | 9/2011 | Bonsignore et al. | |
| 2016/0244756 A1 | 8/2016 | Baryza et al. | |

* cited by examiner

CANNULA CUT STENT WITH CLOSED END CELL GEOMETRY

BACKGROUND

The present application generally relates to medical devices. More particularly, the present application relates to devices for implantation within a body vessel, such that the body vessel is supported and kept open.

Many cannula cut intraluminal support devices on the market at present have an open cell geometry so that these devices are flexible enough to conform to the shape of the vessel in which they are to be implanted, and to have good properties with regard to fatigue life. These devices, though, can experience non-uniform deployment when delivered percutaneously. In some cases, the devices can be misaligned, have a distortion of the geometry, or have various portions of the device protrude. End rings in particular may be more susceptible to this type of issue because they only neighbor another ring on one side.

Both self-expanding and balloon-expandable support devices can exhibit this problem of non-uniform deployment. In the case of a balloon-expandable device, the non-uniformity may be seen as a result of the crimping process when the device is placed over a balloon, compressed, and packaged in advance of delivery.

It has been a challenge to develop an intraluminal support device which minimizes or eliminates the problem of non-uniform delivery from the compressed state to the expanded state.

SUMMARY

In one aspect, the present disclosure provides an intraluminal support device for implantation into a lumen of a body vessel. The intraluminal support device may include a tubular body having a first end extending to a second end and defining a longitudinal axis. The tubular body may include a plurality of inner rings each comprising a plurality of struts and bends arranged in a repeating pattern to define a plurality of peaks and a plurality of valleys. The plurality of inner rings may be disposed axially along the longitudinal axis. The tubular body is radially expandable from a compressed state to an expanded state. The support device includes an end cell disposed at one or both of the first end and the second end. The end cell includes a penultimate ring and an ultimate ring. Each of the penultimate ring and the ultimate ring may include a plurality of struts and bends arranged in a repeating pattern to define a plurality of peaks and a plurality of valleys. Each peak of the ultimate ring may be connected at an inner edge thereof to a peak of the penultimate ring at an outer edge thereof by a connector segment. Each valley of the ultimate ring may be connected at an outer edge thereof to a valley of the penultimate ring at an inner edge thereof by a connector segment.

In another aspect, the present disclosure provides an intraluminal support device for implantation into a lumen of a body vessel. The intraluminal support device may include a tubular body having a first end extending to a second end and defining a longitudinal axis. The tubular body may include a plurality of inner rings each made up of a plurality of struts and bends arranged in a repeating pattern to define a plurality of peaks and a plurality of valleys. Each peak of the plurality of inner rings may have a first width. The plurality of inner rings may be disposed axially along the longitudinal axis. The tubular body may be radially expandable from a compressed state to an expanded state. The device may include an end cell disposed at at least one of the first end and the second end, or at one or both of the first end and the second end. The end cell may include a penultimate ring and an ultimate ring. Each of the penultimate ring and the ultimate ring may include a plurality of struts and bends arranged in a repeating pattern to define a plurality of peaks and a plurality of valleys. Each peak of the ultimate ring may be connected at an inner edge thereof to a peak of the penultimate ring at an outer edge thereof by a connector segment. Each peak of the ultimate ring may have a second width less than the first width. Each valley of the ultimate ring may be connected at an outer edge thereof to a valley of the penultimate ring at an inner edge thereof by a connector segment. Each connector segment may be substantially parallel to the longitudinal axis in the compressed state. The intraluminal support device may be self-expanding.

Further objects, features and advantages of this system will become readily apparent to persons skilled in the art after a review of the following description, with reference to the drawings and claims that are appended to and form a part of this specification.

DETAILED DESCRIPTION

The drawings are purely schematic illustrations of various aspects of the invention and are not necessarily to scale, unless expressly stated.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part.

Cannula-cut intraluminal support devices have been used for stabilizing body vessels into which they are implanted, holding the body lumen open and allowing for flow of fluid (such as blood) therethrough. One type of support device or stent includes a plurality of rings disposed coaxially with each other and arranged about a longitudinal axis. Each ring individually comprises a plurality of struts and bends arranged to form a series of peaks and valleys. In some cases, the rings are positioned such that one ring has its peaks aligned with the respective peaks of an adjacent ring, and in some cases, with all other rings of the device to define an in-phase relationship. Devices of this construction may have an advantage for collapse the device so that it can be placed in a delivery system with optimal packing efficiency, so that it can be delivered to a body vessel.

The rings may be connected together with connecting segments. The geometry of the rings and connecting segments (or tie-bars) give the device its physical characteristics in part. Both self-expanding and balloon-expandable intraluminal support devices have been made with this strut architecture.

The struts may be modified to impact radial stiffness of portions of the device. It is to be understood that radial stiffness is the property of a tubular device which dictates the production of radial force when that device is implanted in a body vessel. Radial stiffness is determined by the ability of a cylindrical member to resist a compressive force applied perpendicular to the surface of the cylinder. In order to avoid stressing portions of the body vessel disproportionately, it may be desirable to have a consistent radial stiffness generated across the length of the device.

Each intraluminal support device of this design, whether a self-expanding or a balloon-expandable device, is compressed into a delivery system, introduced to the body vessel at the compressed diameter, and expanded (either passively, in the case of the self-expanding device, or by inflation of an assisting device, such as a balloon catheter) to the physiologically-relevant diameter. Consistent deployment is desirable, as misaligned devices can be difficult to retract and redeploy.

Figure 1A:
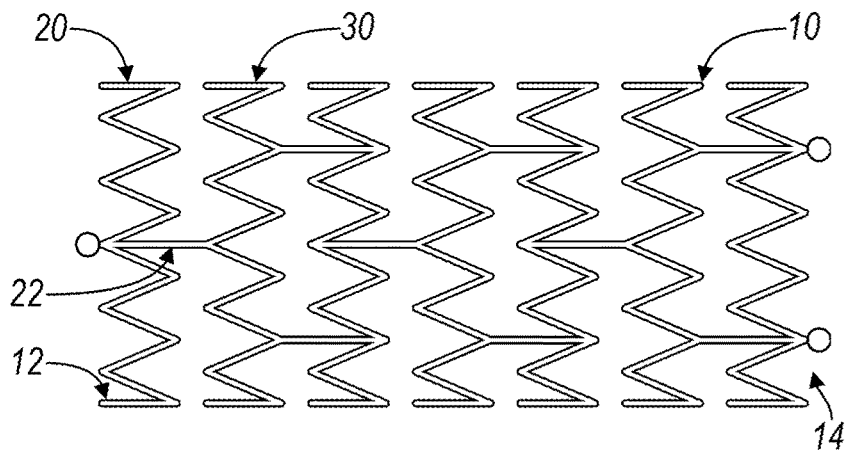
FIG. 1A is a side view of a self-expanding intraluminal support device of the prior art.

FIG. 1A illustrates a self-expanding intraluminal device 10 of the prior art. The device extends from first end 12 to second end 14 and is shown in an ideal expanded state. The ring structure of the device includes an ultimate ring 20 at the first end 12, a penultimate ring 30 adjacent and connected to the ultimate ring 20, and a plurality of inner rings. The rings are connected by a plurality of tie bars 22.

Figure 1B:
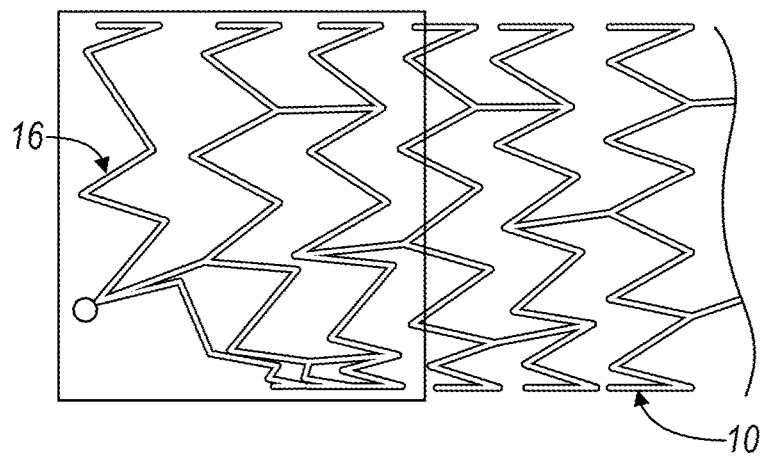
FIG. 1B is a partial side view of the intraluminal support device of FIG. 1A showing its unevenly deployed state at one device end.

FIG. 1B shows the device 10 of FIG. 1A after deployment from the contracted state. The structure demonstrates uneven expansion 16, in which the ultimate ring 20 and penultimate ring 30, as well as a portion of the inner ring structure, have become distorted. The device 10 in its entirety does not match the cylindrical profile of the device in its ideal state.

Figure 2A:
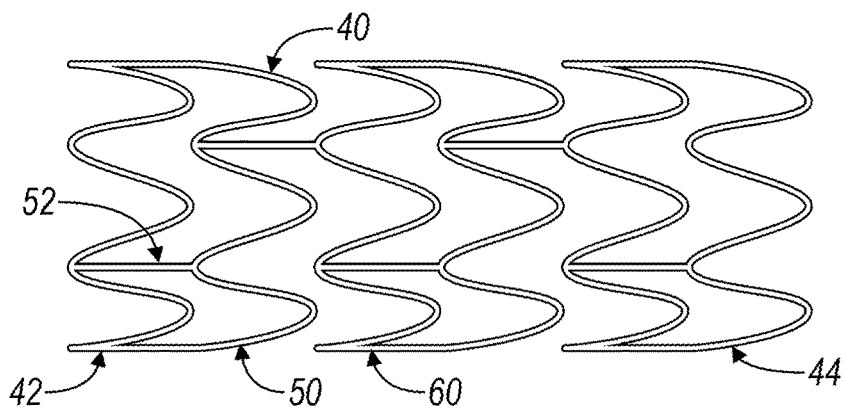
FIG. 2A is a side view of a prior art balloon-expandable intraluminal support device in its expanded state.

FIG. 2A illustrates a balloon expandable intraluminal support device 40, or stent, of similar construction. The device 40 extends from first end 42 to second end 44 and includes ultimate ring 50 and penultimate ring 60, as well as inner ring structures. The rings of the device are connected by tie bars 52.

Figure 2B:
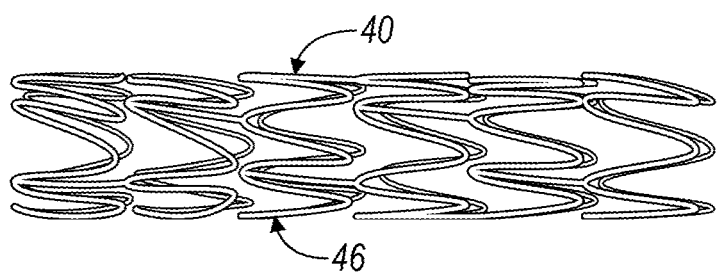
FIG. 2B is a side view of the device of FIG. 2A in its compressed or crimped state.

FIG. 2B illustrates the device of FIG. 2A in a compressed state. In this case, the crimping process has led to struts and tie bars that are askew from the typical cylindrical configuration expected. Thus, in all likelihood, when the device 40 is re-expanded and deployed to a body vessel, it will be misaligned relative to the substantially cylindrical form which it would take had compression been correct.

Without wishing to be bound by a particular theory, it is thought that prior art devices 10 and 40 may be susceptible to misalignment during compression or deployment because the structure at the end cells (the ultimate ring, the penultimate ring, and the connectors or tie-bars therebetween) is substantially the same as it is in other regions of the device. That is, the structure involves relatively few tie bars, which increases compressibility and flexibility of the device, but may not provide the requisite structure to dependably convert between the compressed and the expanded state.

Figure 3:
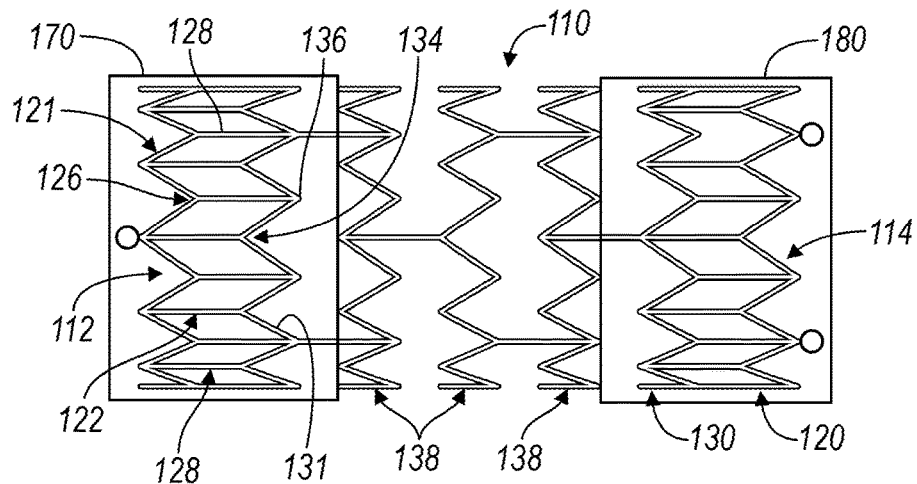
FIG. 3 is a view of a self-expanding intraluminal support device constructed in accordance with the principles of the present disclosure.

FIG. 3 illustrates a self-expanding intraluminal device 110 constructed in accordance with the principles of the present invention. The device 110 extends from first end 112 to second end 114 and comprises a plurality of rings coaxially aligned and longitudinally displaced from one another. The device defines a longitudinal axis A running therethrough.

The device 110 includes a number of different types of rings. The ultimate rings 120 lie at the ends of the device, at first end 112 and second end 114. The penultimate rings 130 lie interior to the ultimate rings 120, and together with the ultimate rings 120, define end cells 170 for the device 110.

The end cells 170 have a closed-cell structure due to the abundance of connectors 122, 128 joining the ultimate ring 120 to the penultimate ring 130.

The rings of the device 110 are arranged as a plurality of struts and bends that give rise to a zigzag shape, appearing like a series of Vs connected together. The alternating, zigzag fashion means that the bends of the device are considered peaks and valleys. Whether a bend is considered a peak or a valley may be dependent on the perspective of the viewer, specifically whether the viewer is considering the device from the first end or from the second end. When an end is chosen, the bends of an ultimate ring of the device that define the extreme endpoints of the device are considered peaks, and the bends positioned between the peaks are considered valleys. This designation propagates to the other end of the device. Because of the symmetric nature of some embodiments of the device of the present disclosure, the bends defined as peaks when viewed from the first end will instead be considered valleys when viewed starting from the second end, and vice versa.

Additionally, each peak and each valley is a bend that has an inner portion and an outer portion. The inner portion of the peak or valley lies circumferentially between the two struts that adjoin the bend, and the outer portion lies longitudinally opposite of the inner edge. The outer edges represent the furthest extents, longitudinally, of the rings.

When adjacent rings have an in-phase relationship of struts and bends, an inner edge of one peak or valley, when attached to the adjacent ring by a tie bar or connector, will be attached to an outer edge of the corresponding structure on the adjacent ring.

The struts 121 and bends of the ultimate ring 120 combine to define a series of peaks 124 and valleys 126 in alternating fashion, as do the struts 131 and bends of the penultimate ring 130. Every peak 122 of the ultimate ring 120 is connected to a peak 132 of the penultimate ring 130 by a peak-to-peak connector 122, and every valley 126 of the ultimate ring 120 is connected to a valley 136 of the penultimate ring 130 by a valley-to-valley connector 128. As can be seen from FIG. 3, the inner rings 138 are connected to the end cells 170 and to each other by connectors, but these are not connected at every vertex. Thus, the inner rings 138 have an open-cell type of geometry. Connection at each vertex in the end cells 170 increases the axial stiffness of the device at that position and leads to consistent expansion and deployment to a substantially cylindrical device. Adding more connectors increases axial stiffness, which is desirable for not only deployment, but also loading of a self-expanding device. The increase in axial stiffness makes crimping more stable and aids in pushing the device out of the compression device (such as a crimper), assisting in loading the device into a delivery system by transferring axial (that is, pushing) force more effectively to the neighboring cell. Such a construction may create a discontinuity in the axial stiffness along the length of the device, but only negligibly so, and this discontinuity is outweighed by the benefit with regard to even expansion realized during deployment.

The rings 120/130/138 of the device 120 of FIG. 3 are shown in an in-phase relationship. Such a relationship allows for the inclusion of relatively short and straight connectors or tie-bars between the penultimate ring 130 and the ultimate ring 120. Such a connector arrangement, in combination with the in-phase arrangement of the peaks and valleys, allows for increased axial stiffness due to a minimal cantilever phenomenon, and therefore increases control of expansion of the end cell of the device.

In other embodiments, however, the inner rings 138 need not be in-phase with one another or with the penultimate ring 130. However, having rings in phase with each other allows the connectors between two in-phase rings to be substantially parallel to the longitudinal axis when in the compressed configuration. Additionally, in-phase rings may pack more efficiently when collapsed, as peaks of one ring may lie within valleys of its adjacent ring. In another embodiment, the connectors need not be straight, or parallel to the longitudinal axis. The connectors may be curved (into an S shape or U shape, among others), or kinked. In another embodiment, the connectors may connect at circumferentially-offset locations on the adjacent rings. An embodiment in which each connector which connects the ultimate ring to the penultimate ring in such a way that compression of the device is readily achieved will be favored. One such embodiment involves tie bars that are parallel to the longitudinal axis; each of these may be referred to as a straight segment. However, other designs are possible so long as compression is accommodated.

Although FIG. 3 illustrates a device having a closed end cell structure at each of the first end 112 and the second end 114, it will be appreciated that in certain embodiments, the device may have a closed end cell on only one end.

Figure 4:
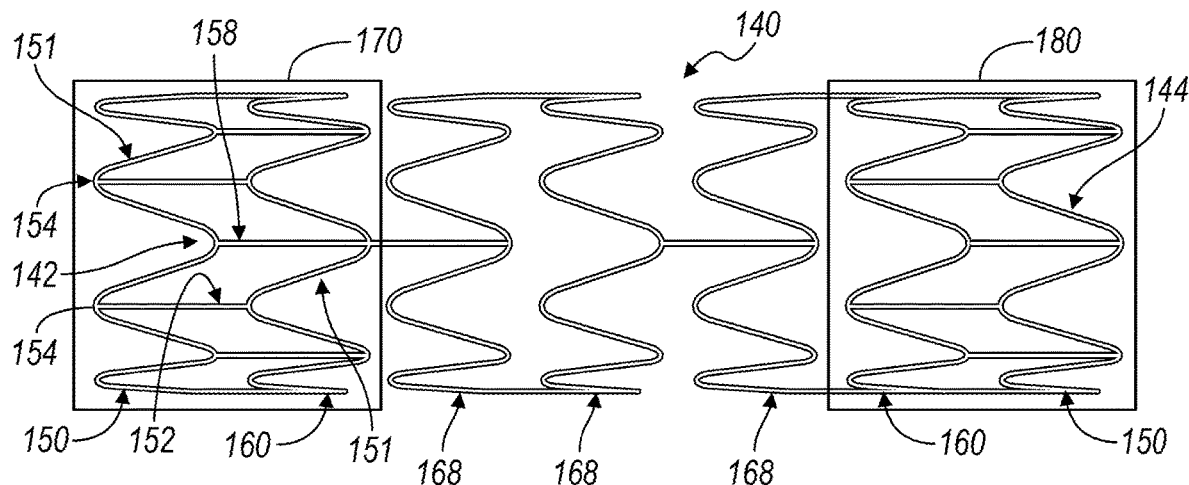
FIG. 4 is a view of a balloon-expandable intraluminal support device constructed in accordance with the principles of the present disclosure in its expanded state.
Figure 5:
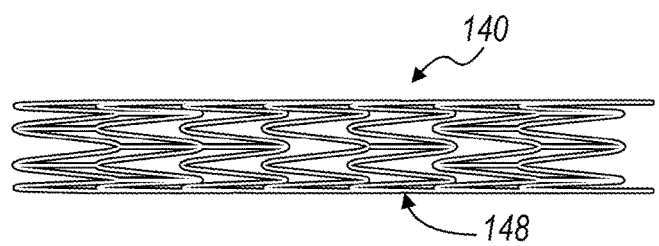
FIG. 5 is a view of the device of FIG. 4 in the compressed state.

FIG. 4 presents another intraluminal support device 140 constructed in accordance with the embodiments of the present disclosure. Device 140 is a balloon-expandable support device with a similar construction to the self-expanding device 110 of FIG. 3. The device 140 extends from first end 142 to second end 144 and includes ultimate rings 150, penultimate rings 160, making up end cells 180, as well as inner rings 168, all of which are linked by a plurality of connectors. The ultimate ring 150 includes a plurality of struts 151 and bends arranged to form an alternating pattern of peaks 154 and valleys 156. Similarly, penultimate ring 160 includes a plurality of struts 161 and bends to form an alternating pattern of peaks 164 and valleys 166, which are aligned in-phase with the peaks 154 and valleys 156 of ultimate ring 150. The ultimate ring 150 is connected to penultimate ring 160 via a plurality of peak-to-peak connectors 152 and valley-to-valley connectors 158. As shown in FIG. 5, such an arrangement, with a closed end-cell structure, allows for an evenly-crimped configuration 148, even with the inner rings 168 having an open-cell configuration.

Such designs, with tie-bar connectors attaching each peak to each peak at the ends of the device, and each valley to each respective valley, have not been pursued previously, possibly because the increased number of tie bars at the ends of the device lead to an increased quantity of metal at the tips of the device (specifically, the peaks, such as peak 154 of ultimate ring 150), which leads to an increase in radial force at the end of the device 110. This increase in radial force can be disadvantageous in certain applications. It is preferred to have an even radial force profile across the length of the device. That is, even with an increased number of tie-bar-to-peak intersections at the extreme end of the device, this portion of the device should generate radial force substantially equal to that generated by the inner rings 168.

Figure 6:
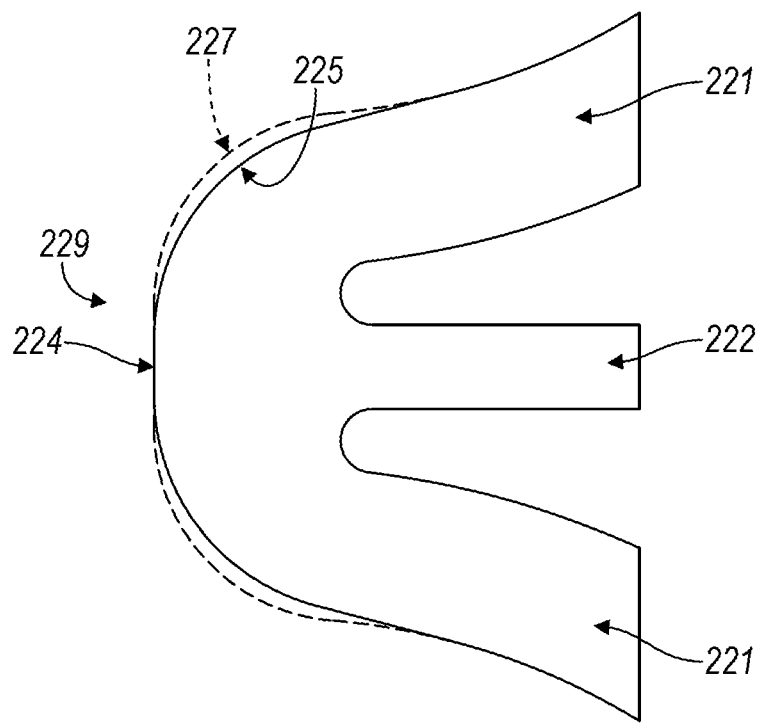
FIG. 6 is a close-up view of an end portion of an end peak of a ring of a device constructed in accordance with an embodiment of the present disclosure.
Figure 7:
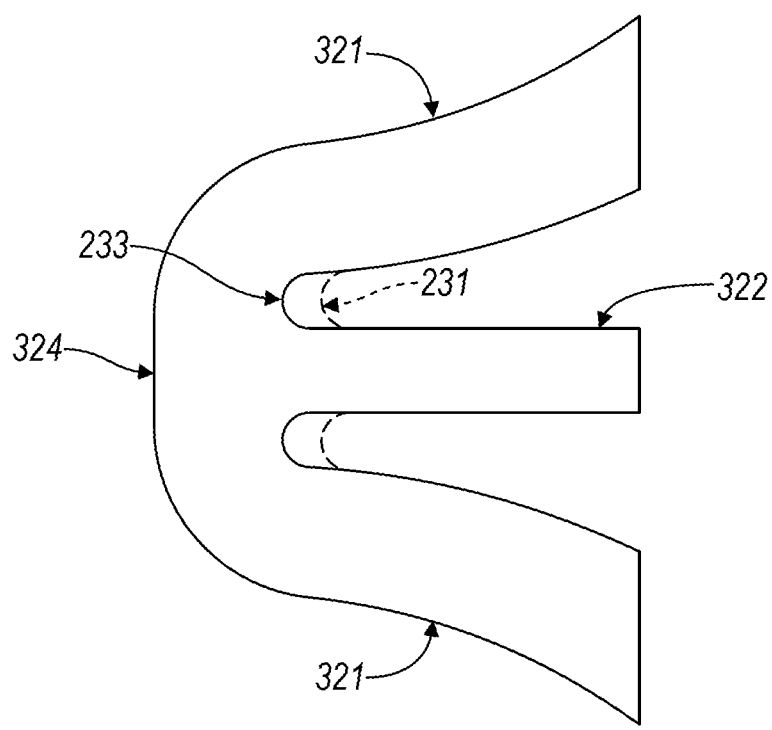
FIG. 7 is a close-up view of an end portion of an end peak of a ring of a device constructed in accordance with another embodiment of the present disclosure.
Figure 8:
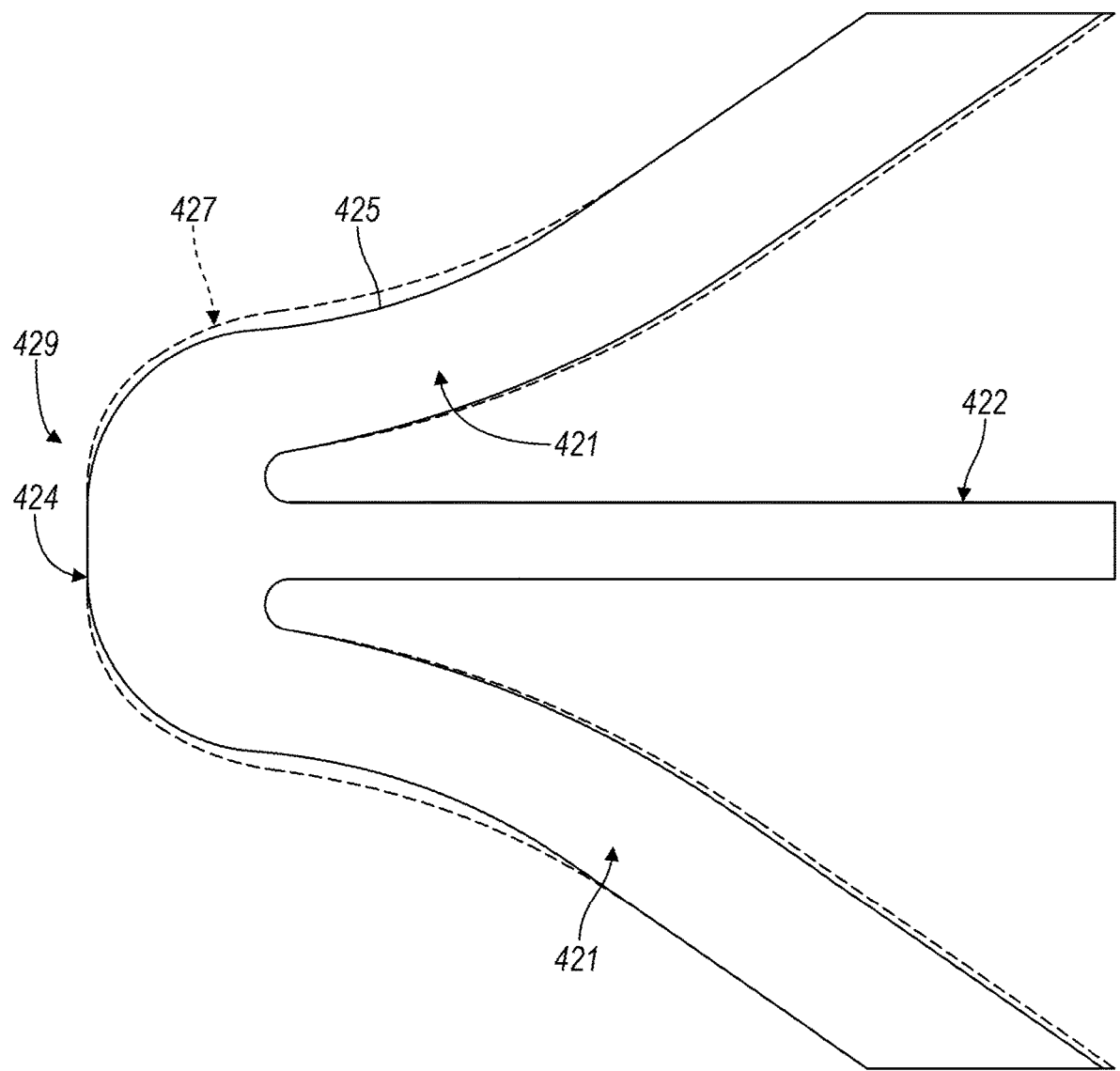
FIG. 8 is a close-up view of an end portion of an end peak of a ring of a device constructed in accordance with another embodiment of the present disclosure.

FIGS. 6-8 illustrate end structures that reduce the radial force generated at tips of the end cell. FIG. 6 shows a peak 224 of an ultimate ring 220 and the peak-to-peak tie bar 222 that connects it to its corresponding penultimate ring. The peak 224 is formed at the junction of two struts 221. The struts 221, converging at peak 224, have an arcuate profile, and prior to modification, have the same shape as the struts of the inner rings of the device. The peak is thinned from its original contour 227 to form the new edge 225 of the strut 221, resulting in tapered tip 229. The thinning of the tip or peak results in a smaller amount of metal in the peak region, leading to an overall radial force profile that matches that of the inner rings.

FIG. 7 demonstrates a second method of radial force adjustment. Rather than cutting away the outer edge of the peak as in FIG. 6, the structure of FIG. 7 has a cutaway region internal to and abutting the tie bar 322. The struts 321 thinned internally from their original contour 231, the tip thickness being reduced to the cut configuration 233.

FIG. 8 illustrates another peak 424 which is narrowed in comparison to the peaks of the inner rings of the device. In this embodiment, the struts 421 of the peak are pre-cut at the time of manufacture of the support device from the precursor cannula to provide a wider gap between the tie bar 422 and the inner edge of the struts 421. The outer edge of the strut 421 is also thinned from original contour 427, representing the structure of a typical strut of an internal ring, to modified profile 425, which leads to less accumulated metal at the tapered tip 429.

In one embodiment, the struts of the device typically have a width of about 195 microns. In this embodiment, the peaks of the end cells are cut or tapered so that the width of the struts is tapered to a width of about 175 microns at the peak. In some embodiments, the width of the struts at the peak may be about 80%, or about 85%, or about 90%, or about 95%, or any quantity between 80% and 95% inclusive, of the typical width of the struts of the device.

In certain embodiments, it may be beneficial to thin the outer edge of the struts (as seen in FIGS. 6 and 8) rather than solely the inner edge (as seen in FIG. 7). A cannula-cut self-expanding intraluminal support device as disclosed herein generally undergoes multiple heat-setting steps. A cannula-cut balloon-expandable intraluminal support device as disclosed herein generally undergoes expansion when a balloon is inflated in vivo. A thinner component, such as at the inner junction of the struts and a tie-bar connection, may represent a point of potential fracture during the manufacture of a self-expanding device, or expansion of a balloon-expandable device. Therefore, cutting away the material at the outer edge may be advantageous, although the scheme of FIG. 7 also allows for increasing the density of tie bars between peaks and valleys of ultimate rings and penultimate rings in accordance with the principles of the present disclosure.

Self-expanding devices according to the present disclosure may be made by cutting a cannula of shape memory metal or any other elastic-plastic material, such as with a laser, to form the strut and bend structure. The struts and bends can be formed with an arcuate profile in order to avoid sharp edges, and a teardrop shaped gap can be formed at peaks and at valleys where a tie bar meets the peak or valley in order to meet tolerances of the device. The slot width of the laser beam can be selected to give a cut of the proper dimensions. After cutting, the self-expanding device may be placed over a cylindrical mandrel and heat set at least one time, but generally multiple times (such as five or six iterations) in order to generate a remembered state of the shape memory metal. The device may then be electropolished in order to further smooth the device. In the case of a device which has thinner peaks at the end cells than in the inner rings, the thinned portions of the peaks may be formed in the initial cut pattern, in a second laser cutting step, by selectively electropolishing to the desired width, or a combination of any of the preceding.

A device in accordance with the principles of the present invention may further incorporate radiopaque markers to assist a physician with placement in the body. Many suitable radiopaque materials are known and any of these may be selected for use with a device of the present disclosure. The radiopaque markers may be made of materials including gold, palladium, tantalum, platinum, and biocompatible alloys of any of these materials.

A device may be of unitary construction. In one sense, a device of unitary construction is made of a single piece of precursor material. One particular example of a device of unitary construction is one that is cut from a cannula. Specifically, a cannula of a shape-memory metal such as a nickel-titanium alloy may be laser-cut to yield the device.

A device in accordance with the principles of the present disclosure may be made according to a series of steps. As mentioned previously, a single, monolithic, unitary tube of a shape memory alloy may be precisely laser cut to generate the overall shape of the struts and connectors of the device.

A method of using a device as described in the instant disclosure can include a number of different steps. In the case of a self-expanding device, one step, the intraluminal support device may be compressed to a compressed state and loaded into a delivery assembly. The delivery assembly may be introduced to the body, possibly percutaneously, and the device delivered, such as by a pusher, into the body lumen in need of treatment. The device, upon deployment, will anchor against the lumen (or vessel) wall at its expanded diameter. In the case of a balloon-expandable device, the device will be crimped or compressed over the inflatable balloon of a balloon catheter, and loaded into a delivery assembly. The device will be placed in the lumen of the body vessel at the intended target location, the balloon expanded until the device is patent with the wall of the vessel, and the balloon then deflated and the delivery assembly withdrawn, leaving the device implanted in the body vessel. Delivery may be guided by imaging which may optionally include monitoring of one or more radiopaque portions included on the device.

As a person skilled in the art will readily appreciate, the above description is meant as an illustration of implementation of the principles this application. This description is not intended to limit the scope of this application in that the system is susceptible to modification, variation and change, without departing from the spirit of this application, as defined in the following claims.

What is claimed is:

1. An intraluminal support device for implantation into a lumen of a body vessel, the intraluminal support device comprising:
    a tubular body having a first end extending to a second end and defining a longitudinal axis, the tubular body comprising a plurality of inner rings each comprising a plurality of struts and bends arranged in a repeating pattern to define a plurality of peaks and a plurality of valleys, the plurality of inner rings being disposed axially along the longitudinal axis, the tubular body being radially expandable from a compressed state to an expanded state; and
    an end cell disposed at at least one of the first end and the second end, the end cell comprising a penultimate ring and an ultimate ring, each of the penultimate ring and the ultimate ring comprising a plurality of struts and bends arranged in a repeating pattern to define a plurality of peaks and a plurality of valleys, each peak of the ultimate ring having a width less than that of a peak of an inner ring and being connected at an inner edge thereof to a peak of the penultimate ring at an outer edge thereof by a connector segment, and
    each valley of the ultimate ring being connected at an outer edge thereof to a valley of the penultimate ring at an inner edge thereof by a connector segment.

2. The intraluminal support device of claim 1, wherein each of the plurality of inner rings are connected to one another by at least one connector segment.

3. The intraluminal support device of claim 1, wherein each of the connector segments are substantially parallel to the longitudinal axis in the compressed state.

4. The intraluminal support device of claim 1, wherein the intraluminal support device is self-expanding.

5. The intraluminal support device of claim 4, wherein the intraluminal support device comprises a shape-memory material.

6. The intraluminal support device of claim 5, wherein the shape memory material comprises a nickel-titanium alloy.

7. The intraluminal support device of claim 5, wherein the tubular body and the end cell are of unitary construction.

8. The intraluminal support device of claim 7, wherein the tubular body and the end cell are cut from a cylindrical body.

9. The intraluminal support device of claim 1, comprising an end cell at the first end and at the second end.

10. The intraluminal support device of claim 1, wherein each of the plurality of struts of the ultimate ring comprise a taper proximate the peaks.

11. The intraluminal support device of claim 10, wherein the end cell has a radial stiffness substantially equal to that of an inner ring.

12. The intraluminal support device of claim 1, wherein the intraluminal support device is balloon-expandable.

13. An intraluminal support device for implantation into a lumen of a body vessel, the intraluminal support device comprising:
    a tubular body having a first end extending to a second end and defining a longitudinal axis, the tubular body comprising a plurality of inner rings each comprising a plurality of struts and bends arranged in a repeating pattern to define a plurality of peaks and a plurality of valleys, each peak of the plurality of inner rings having a first width, the plurality of inner rings being disposed axially along the longitudinal axis, the tubular body being radially expandable from a compressed state to an expanded state; and
    an end cell disposed at at least one of the first end and the second end, the end cell comprising a penultimate ring and an ultimate ring, each of the penultimate ring and the ultimate ring comprising a plurality of struts and bend arranged in a repeating pattern to define a plurality of peaks and a plurality of valleys, each peak of the ultimate ring being connected at an inner edge thereof to a peak of the penultimate ring at an outer edge thereof by a connector segment, each peak of the ultimate ring having a second width less than the first width, each valley of the ultimate ring being connected at an outer edge thereof to a valley of the penultimate ring at an inner edge thereof by a connector segment, each connector segment being substantially parallel to the longitudinal axis in the compressed state, wherein the intraluminal support device is self-expanding.

14. The intraluminal support device of claim 13, comprising an end cell at the first end and at the second end.

15. The intraluminal support device of claim 13, wherein the end cell has a radial stiffness substantially equal to that of an inner ring.

16. The intraluminal support device of claim 13, wherein each of the plurality of struts of the ultimate ring comprise a taper proximate the peaks.

17. The intraluminal support device of claim 13, wherein the intraluminal support device comprises a shape-memory material.

18. The intraluminal support device of claim 13, wherein the tubular body and the end cell are of unitary construction.

19. The intraluminal support device of claim 18, wherein the tubular body and the end cell are cut from a cylindrical body.

20. An intraluminal support device for implantation into a lumen of a body vessel, the intraluminal support device comprising:

a tubular body having a first end extending to a second end and defining a longitudinal axis, the tubular body comprising a plurality of inner rings each comprising a plurality of struts and bends arranged in a repeating pattern to define a plurality of peaks and a plurality of valleys, the plurality of inner rings being disposed axially along the longitudinal axis, the tubular body being radially expandable from a compressed state to an expanded state; and an end cell disposed at at least one of the first end and the second end, the end cell comprising a penultimate ring and an ultimate ring, each of the penultimate ring and the ultimate ring comprising a plurality of struts and bends arranged in a repeating pattern to define a plurality of peaks and a plurality of valleys, each of the plurality of struts of the ultimate ring comprising a taper proximate the peaks, each peak of the ultimate ring having a width less than that of a peak of an inner ring and being connected at an inner edge thereof to a peak of the penultimate ring at an outer edge thereof by a connector segment, and each valley of the ultimate ring being connected at an outer edge thereof to a valley of the penultimate ring at an inner edge thereof by a connector segment.

* * * * *